United States Patent [19]

Tucker

[11] Patent Number: 5,591,913
[45] Date of Patent: Jan. 7, 1997

[54] APPARATUS AND METHOD FOR ULTRASONIC SPECTROSCOPY TESTING OF MATERIALS

[75] Inventor: James R. Tucker, Birmingham, Ala.

[73] Assignee: Southern Research Institute, Birmingham, Ala.

[21] Appl. No.: 241,862

[22] Filed: May 12, 1994

[51] Int. Cl.[6] .................................................. G01N 29/04
[52] U.S. Cl. ................................................ 73/628; 73/602
[58] Field of Search ............................. 73/602, 624, 625, 73/628, 579, 599, 659

[56] References Cited

U.S. PATENT DOCUMENTS

| | | |
|---|---|---|
| 3,224,253 | 12/1965 | McKay . |
| 3,948,345 | 4/1976 | Rosencwaig . |
| 4,271,705 | 6/1981 | Crostack . |
| 4,285,241 | 8/1981 | Smith et al. . |
| 4,428,235 | 1/1984 | Sugiyama . |
| 4,512,194 | 4/1985 | Beuter . |
| 4,539,847 | 9/1985 | Paap . |
| 4,577,503 | 3/1986 | Imaino et al. . |
| 4,581,935 | 4/1986 | Breazeale . |
| 4,704,905 | 11/1987 | Arora . |
| 4,758,964 | 7/1988 | Bittner et al. . |
| 4,819,649 | 4/1989 | Rogers et al. ........................ 73/624 |
| 4,829,823 | 5/1989 | Michel . |
| 4,949,313 | 8/1990 | Iwasawa . |
| 5,062,296 | 11/1991 | Migliori . |
| 5,099,848 | 3/1992 | Parker et al. ........................ 73/575 |
| 5,191,795 | 3/1993 | Fellingham et al. ................ 73/599 |
| 5,303,590 | 4/1994 | Modderman et al. . |
| 5,426,979 | 6/1995 | Kantorovich et al. ............... 73/628 |

Primary Examiner—Richard Chilcot
Assistant Examiner—Max Noori
Attorney, Agent, or Firm—Pollock, Vande Sande & Priddy

[57] ABSTRACT

An apparatus and method for performing ultrasonic spectroscopy provides for rapid evaluation of test materials with good amplitude, balanced response at all test frequencies. A swept frequency signal is generated which is applied to a transmit transducer coupled to a test part. A receive transducer provides a detected signal that is fully digitized for real-time or post signal processing. The created swept frequency signal can be equalized from data obtained from direct coupling between transmit and receive transducers. The resultant data is analyzed for amplitude and/or phase information as a function of frequency and can be used to analyze filter characteristics, identify resonances, characterize material signatures and many other applications.

13 Claims, 12 Drawing Sheets

APPARATUS AND METHOD FOR ULTRASONIC SPECTROSCOPY TESTING OF MATERIALS

The present invention relates to a method for ultrasonic spectroscopy testing of materials. Specifically, a system is described for generating a swept acoustic wave which is coupled to a test material, and measuring the resultant frequency response of the test material to the acoustic wave. The prior art techniques for diagnosing materials using a swept frequency ultrasonic acoustic wave are illustrated in U.S. Pat. No. 5,062,296. This technology relies upon the generation of a multiple frequency signal such as a swept frequency signal which is coupled to a material being inspected. A receive transducer coupled to the material under test generates an electrical signal proportional to the detected acoustic or ultrasonic wave in the material. These types of systems analyze the acoustic energy detected in the test material.

In the previously-mentioned U.S. Pat. No. 5,062,296, a swept frequency signal is applied to an acoustic transducer which is in turn coupled to a part under investigation. An acoustic detector coupled to the test object produces a signal from the test object and applies it to a square law detector. The square law detector produces a signal which represents the amplitude function of the frequency components of the signal. The phase information of these signal levels is removed and unavailable for analysis. The square law detector output signal is digitized and analyzed to locate resonant response peaks within the frequency spectrum of the signal. The patented technique defines small frequency intervals and generates a swept frequency acoustic signal within each of the intervals and applies the signals to a test sample. The amplitude of signals coupled from the test sample is analyzed over each interval to locate resonant response peaks. The density distribution of the resonant response peaks from these sweep intervals are used to characterize and distinguish test objects from one another.

The swept techniques which generate an acoustic wave having a swept frequency, require a time-based data acquisition. In these techniques, an assignment of amplitude (or attenuation) to a particular frequency requires correlating in time the input swept frequency acoustic signal with the detected swept acoustic signal. An integrator integrates the detected acoustic response during the frequency sweep of the input acoustic signal. The process requires that the sweep occur at a rate such that the time delay induced by the material under test does not interfere with the time correlation between a detected acoustic signal and the applied acoustic signal, or that the output be time-corrected to avoid the consequences of the test material delay. Measurement precision using the swept techniques is inherently limited by the sweep rate.

In a related technology, the device in accordance with U.S. Pat. No. 4,949,313 generates an ultrasonic chirp pulse. In accordance with known signal processing from the radar art, the ultrasonic signal is changed in frequency as a function of time in order to time encode the signal over its duration. A digital representation of the ultrasonic chirp reflected from a known surface is then used for comparison in a pulse compression procedure to spatially analyze a reflected or transmitted acoustic wave from a given object. In this technique, no use is made of the actual frequencies used or their respective amplitudes. Other broadband ultrasonic techniques employ a narrow pulse which, in accordance with Fourier theory, produces a large spectrum of individual frequencies. Such systems are described in "Spectrum Analysis: A New Tool for Quality Control", G. Banella, F. Monti, NBT International, August 1976, Vol. 9, No. 4. However, the narrower pulses tend to produce multiple frequency signal components of a very small amplitude whose detection is limited by system noise.

SUMMARY OF THE INVENTION

It is an object of this invention to provide a system for ultrasonic spectroscopy testing of materials.

It is a more specific object of this invention to produce a signature for a test material based on the frequency response of the material to a swept frequency acoustic signal.

It is yet a more specific object of this invention to analyze a detected acoustic signal without the need for synchronization or correlation with an applied acoustic signal.

These and other objects of the invention are provided for by an apparatus and method which couples a swept frequency acoustic wave to a test material. The swept acoustic signal is generated from a plurality of amplitude values which define a swept wave. The amplitude values are preferably modified to equalize the frequency response of the transmit and receive transducers which are coupled to the test material. Alternatively, the sweep rate can be modified to implement an equalized frequency response.

The amplitude values may be continuously and sequentially supplied to a circuit which produces a swept frequency analog signal from the amplitude value. The analog signal is coupled to a transmit transducer for generating the swept acoustic wave.

In a preferred embodiment of the invention, a receive transducer is coupled to a test material. A signal from the receive transducer is processed to derive a Fast Fourier transform of a detected signal. The Fast Fourier transform is used to identify the test part, or used to assess the quality of the part.

In a preferred embodiment, the created swept frequency signal is generated digitally from an array of angles which define a standing sine wave. The frequency range of the resulting wave is dependent upon the rate of the angle change, the number of points in the particular sine wave cycle and the output rate of a digital to analog converter which creates an analog signal from the sine of the array of angles. These values are "equalized" to compensate for the frequency non-linearity of the transducers. A single readout of the array will generate the desired swept frequency waveform. The processing of the detected frequency signal response can be through any known transform that converts the time domain data to the frequency domain.

DESCRIPTION OF THE DRAWINGS

FIG. 12b shows the arrangement of the transmit and receive acoustic transducers which produces the frequency spectrum of FIG. 12a.

FIG. 13b illustrates the arrangement of transmit and receive transducers 11 and 12 which produces the frequency spectrum of FIG. 13a.

DESCRIPTION OF THE PREFERRED EMBODIMENT

Figure 1:
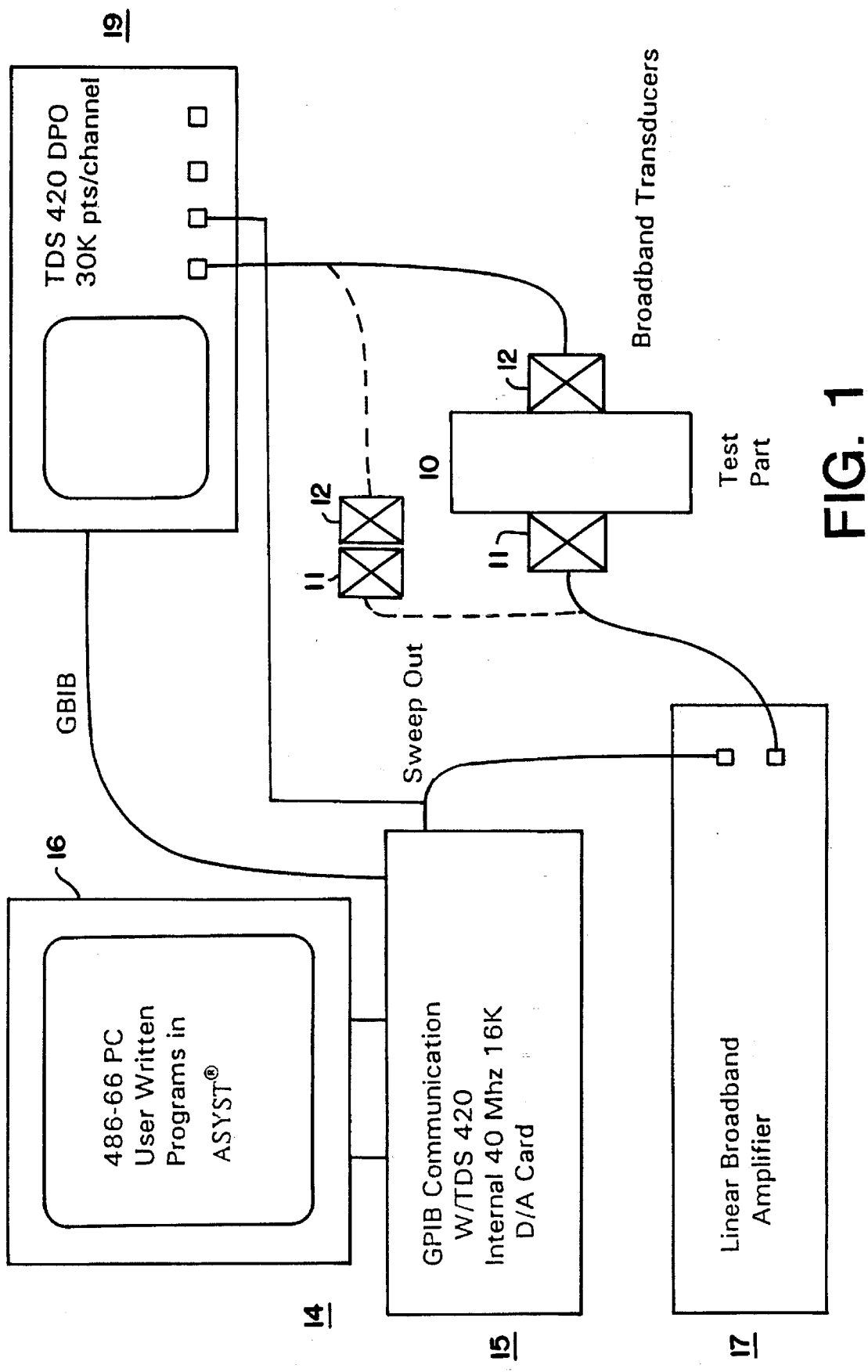
FIG. 1 is an illustration of an apparatus in accordance with a preferred embodiment for measuring the acoustical properties of a test part.

Referring now to FIG. 1, there is shown a test part 10 which is acoustically coupled to two transducers 11 and 12. The transducer 11 is a transmit transducer which will generate and couple an acoustic wave to a test part 10. The transducer 12 is a receive transducer which will detect acoustic energy within the test part 10.

In ultrasonic spectroscopy, the frequency response of the test part 10 serves as a signature for the part and an indication of its quality. Using a digital processing oscilloscope 19, it is possible to conduct any one of a plurality of frequency/time domain processing steps for the signal produced from receive transducer 12.

The acoustic signal coupled by transducer 11 to test part 10 comprises a swept frequency signal. The swept frequency signal is created by the computer 14 which creates an array of discrete amplitude values defining each cycle of a swept frequency signal. The array is continuously and sequentially read out point by point. The resulting series of amplitude values are supplied as an input signal to a digital to analog converter, preferably having an internal digitization rate of 20 MHz to 40 MHz.

The resulting analog signal is amplified in the amplifier 17 before being applied to the acoustic transducer 11.

Figure 6:
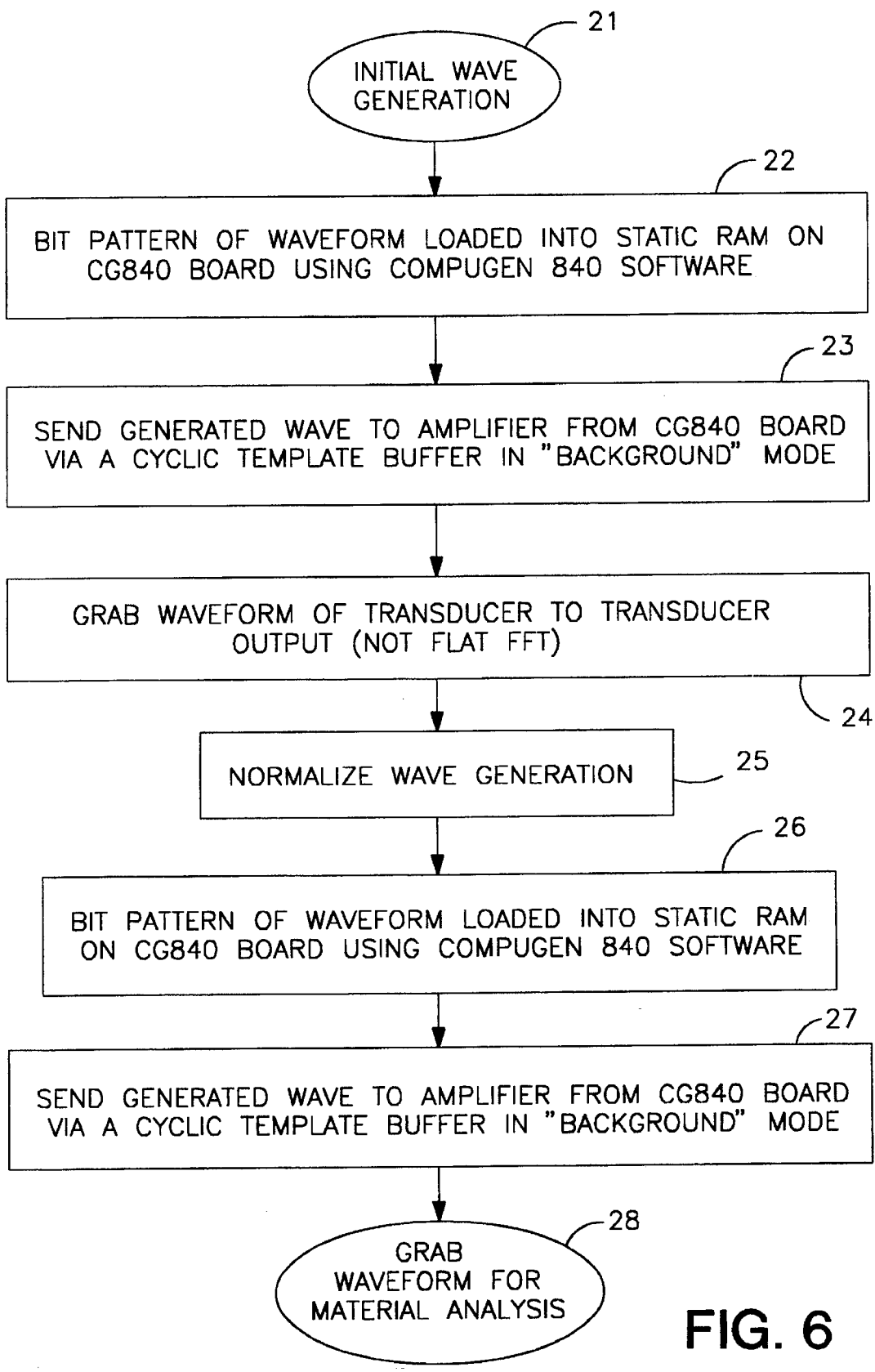
FIG. 6 is a flow chart which shows the process steps for testing a part in accordance with the apparatus of FIG. 1.

As will be apparent in the description of FIG. 6, the swept wave is sent to one of the channels of oscilloscope 19. During testing, a display of the input swept waveform as well as the waveform received from the broadband transducer 12 may be displayed.

The transmit transducer 11 is coupled to the test part 10. Acoustic waves are coupled from the test part 10 to the receive transducer 12. The resulting signal representing the signature for the test part is displayed and stored in the oscilloscope 19.

Figure 2:
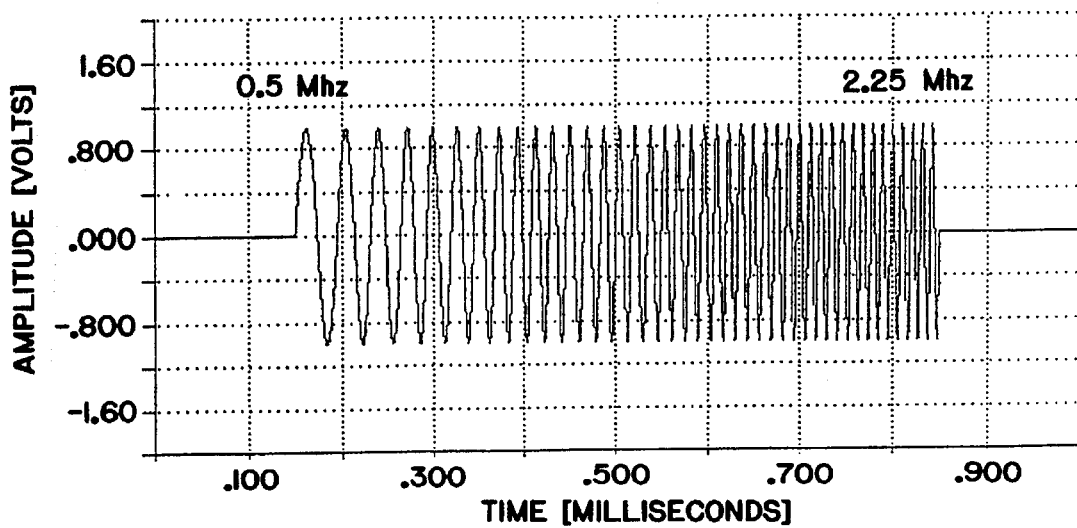
FIG. 2 illustrates the amplitude versus time function of a broad-band spectral acoustic input signal to the test part of FIG. 1.

Referring to FIG. 2, a replica of the acoustic input signal is shown. The signal generally has an amplitude of ±1.0 volts and extends over a frequency spectrum of 0.5 MHz to 2.25 MHz. The entire sweep occurs in approximately 0.8 milliseconds.

Figure 3:
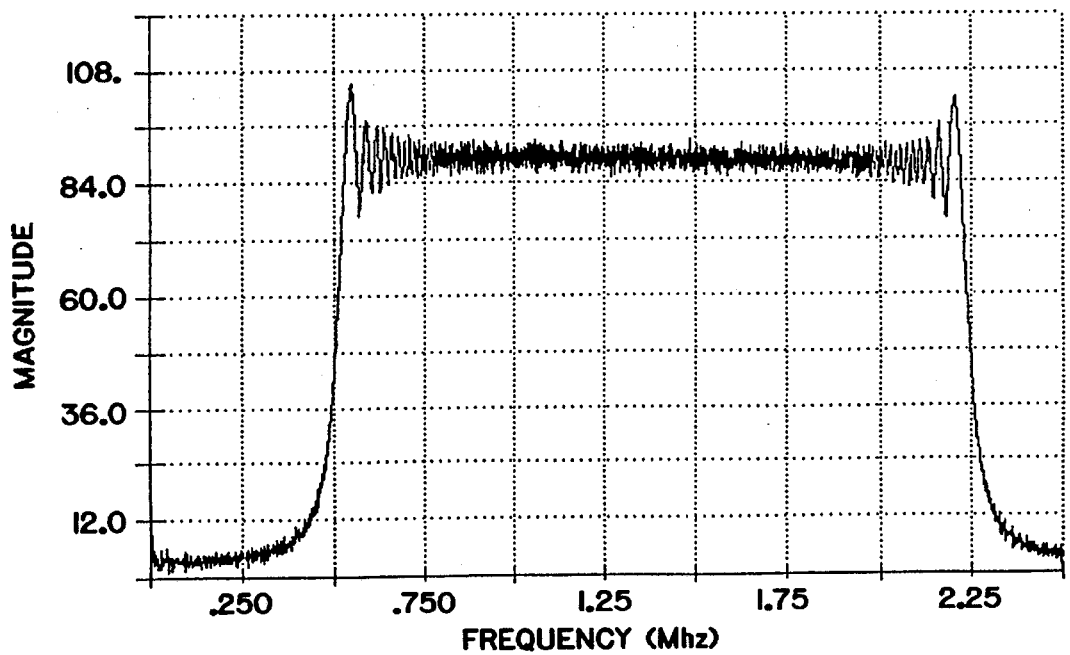
FIG. 3 shows the Fast Fourier transform (FFT) of a test system which has a flat frequency response.

The response shown in FIG. 3 is a Fast Fourier Transform (FFT) for a system which has a uniform gain. Transducers 11 and 12, however, have a respective frequency response which, when combined in the manner of FIG. 1, produces an FFT shown in FIG. 4. Therefore, before testing can commence, the transducers 11 and 12 are shown connected in the dotted line circuit so that an equalization function may be derived for linearizing the FFT response of FIG. 4 to approach that of FIG. 3.

Figure 5:
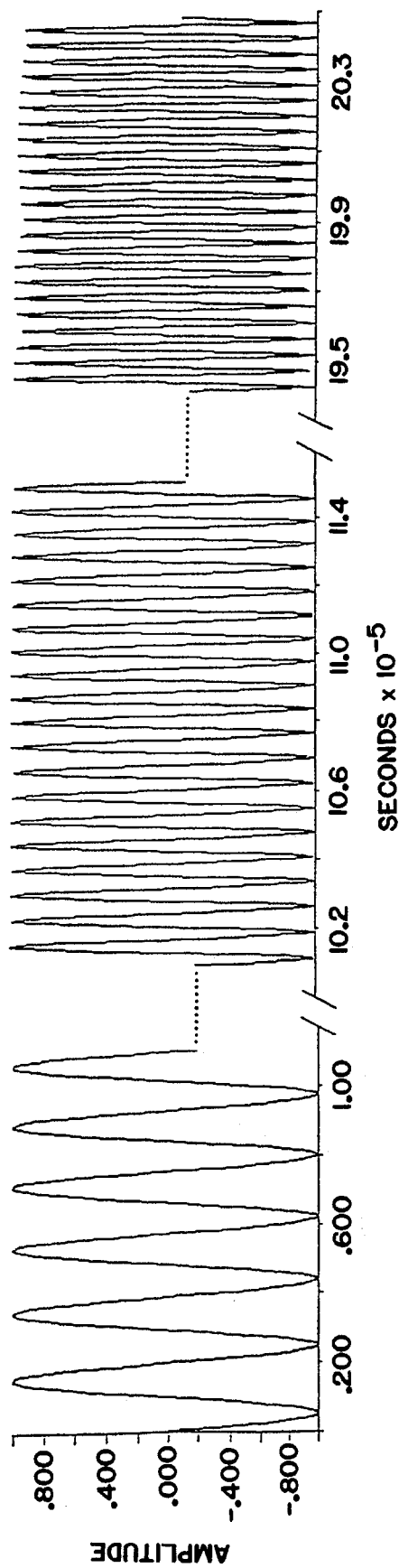
FIG. 5 illustrates the digital creation of a swept acoustic signal from a plurality of data points having a bandwidth between 0.5 MHz and 2.25 MHz.

The sweep frequency signal is shown more particularly in FIG. 5. As will be described with respect to FIGS. 6, 7 and 8, the swept frequency signal is synthesized digitally under control of the computer 14 which may be a personal computer of the type 486–66 or equivalent.

Figure 4:
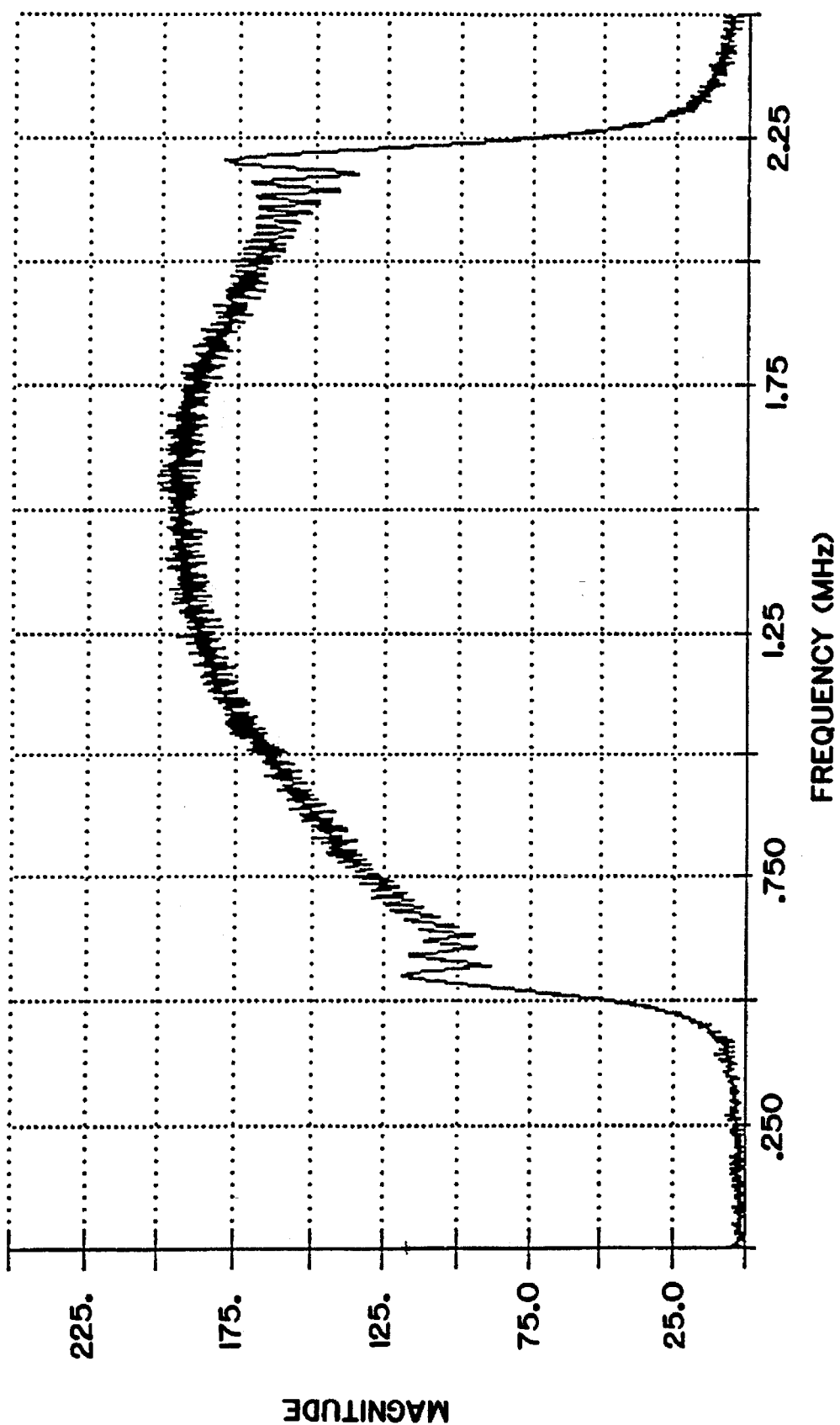
FIG. 4 illustrates a Fast Fourier transform of a broad band spectral acoustic input signal when directly coupled to a receive transducer demonstrating the necessity for equalization of the transmit and receive transducers response.

During both the equalization step, as well as during the recording of actual signal data from the test part, the oscilloscope 19 will store the respective signals received from the receive transducer 12. Under control of the software running in the computer 14, this stored data is grabbed by the communication interface 15, which may be a IEEE 488 interface, also known as GPIB (general purpose interface bus) interface to those skilled in the art, and forwarded to the computer 14 for post-signal processing. The post signal processing may include a Fast Fourier Transform, as is shown in FIGS. 3 and 4.

Having generally demonstrated the apparatus for carrying out the preferred embodiment, reference is now made to FIG. 6 which is an overall block diagram illustrating the steps utilized to produce a signature for test part 10. A first block 21 represents the initial swept acoustic wave generation. As will be described in greater detail with regard to FIG. 7, this step creates an array of data which, in the preferred embodiment, constitutes 12,000 amplitude values defining the swept wave. At this point of the process, the wave is not equalized.

The bit pattern representing the swept wave is loaded into the static RAM of the digital to analog card 15 in the computer 14, using for instance the COMPUGEN 840 software, which is available to computer programmers. Under a command issued by the program 14, the bit pattern is periodically converted to an analog signal by the digital to analog converter 15. The command is generated by a template buffer task in the program operating in the background mode. The generated analog signal is available for display on channel 2 of the oscilloscope.

The frequency swept signal is also applied to the linear broadband amplifier 17. The amplifier is, in turn, connected to the transmit transducer 11. At this portion of the testing sequence, the transmit transducer 11 and receive transducer 12 are coupled directly together, as shown in the broken line circuit of FIG. 1, in order to determine the frequency response of the test set up including two transducers 11, 12, amplifier 17 and connecting cables. In many applications, the major contribution to system non-linearity results from the transducer's frequency response. The signal received on channel 1 of the oscilloscope 19 is thereafter available for analysis. As was evident with respect to FIG. 4, this signal will indicate the degree to which the sweep frequency signal must be normalized in order to provide an equalized response from transducers 11 and 12.

The IEEE 488 communications module 14 will grab or retrieve the stored signal of channel 1 in step 24 and store it utilizing an ASYST program into an ASYST format data file for future use. Fast Fourier Transform analysis may be made by the computer 14 on the contents of the ASYST file. As will be evident from the description of FIG. 8, a normalized swept frequency signal is generated in step 25, which will be applied to the test part 10 during a subsequent measurement interval.

The normalized swept frequency signal comprises a modification of the array created in step 21, the modified bit pattern of the array being stored in step 26 in the static RAM of the digital to analog card 15. The normalized swept frequency signal is then applied via the linear broadband amplifier 17 to the transmit transducer 11. The transmit transducer 11 couples the resulting acoustic signal to the test part 10. The test part 10, in turn, couples an acoustic signal to the receive transducer 12. The input signal is also received by oscilloscope 19 for display.

Oscilloscope 19 also restores the resulting signal as a digitized array of signal values. The array is retrieved by the IEEE 488 communications interface in the computer 14, where it is available for post-processing by computer 14.

The post-processing of the retrieved waveform may include a Fast Fourier Transform analysis of the waveform. The resulting Fast Fourier Transform may be displayed on the computer display 16.

Figure 7:
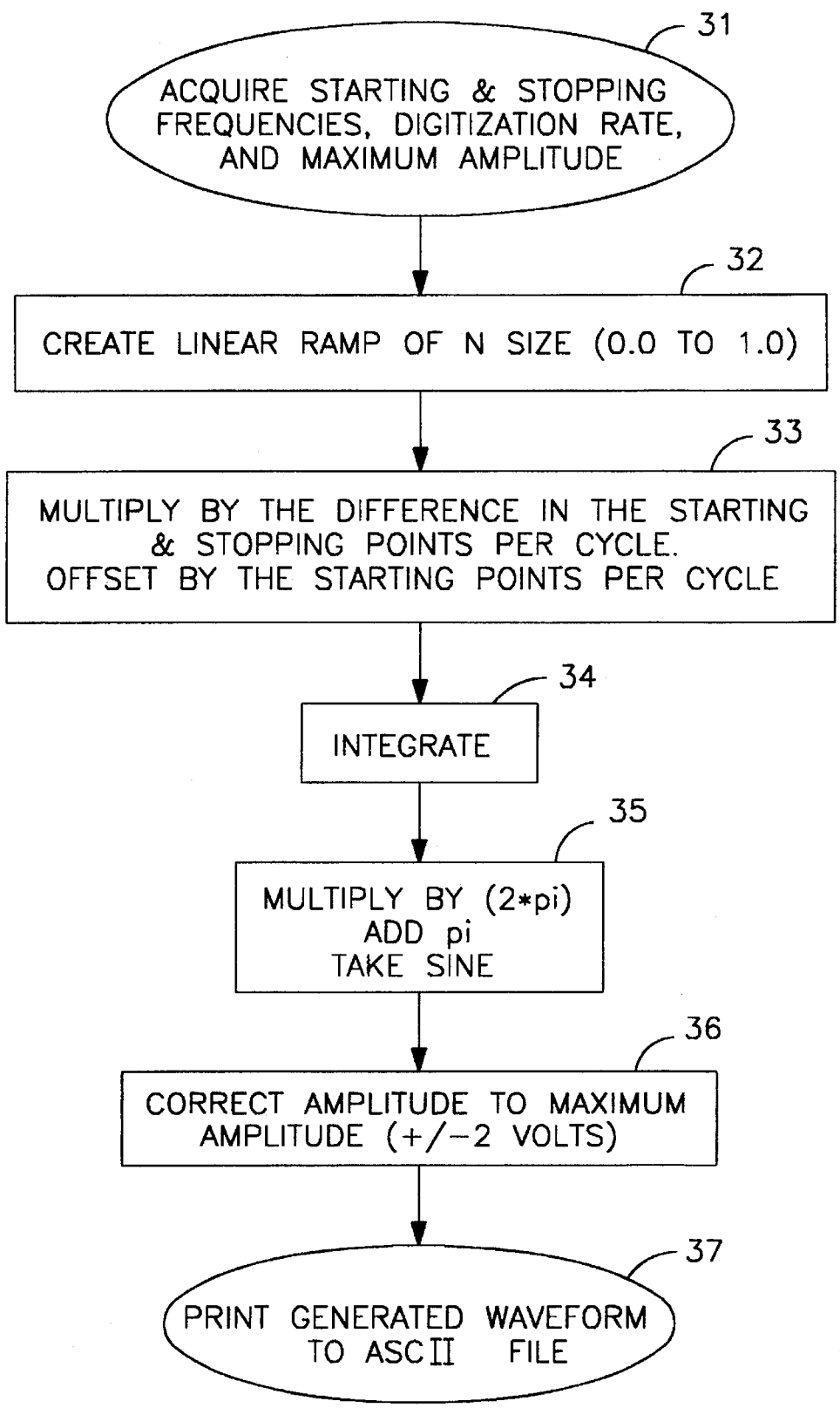
FIG. 7 shows steps to implement the initial acoustic wave generation 21 of FIG. 6.
Figure 8:
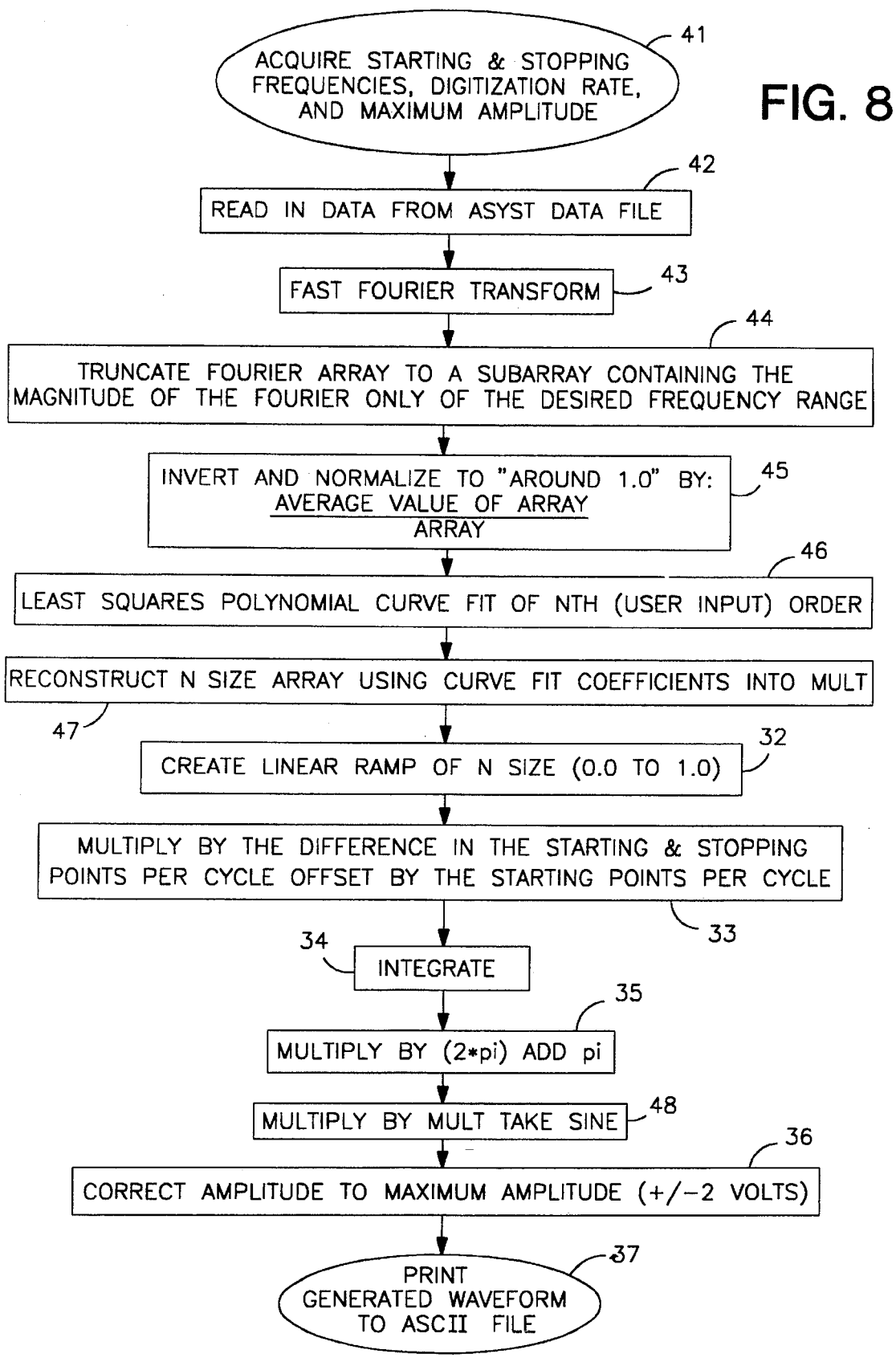
FIG. 8 illustrates the steps to NORMALIZE the swept frequency acoustic wave which equalizes the transmit and receive transducer response of FIG. 1.

The process of generating a swept frequency signal is shown more particularly in FIG. 7. FIG. 7 contemplates the creation by computer 14 of an array of data points constituting the swept waveform.

The beginning step 31 requires that the user select a starting and stopping frequency for the swept waveform, a digitization rate representing the digital to analog converter speed in the D to A card in the computer 15, and a maximum amplitude for the swept signal. Once the user has selected and entered these parameters, a linear ramp of size N is created having values 0.0 to 1 in step 22. For the swept waveform of FIGS. 2 and 5, the size N is approximately 12,000 points. Values of 0.0 to 1 for the ramp are entered in an array in step 32.

From the linear ramp represented by the data created in step 32, a function represented by $$\sin\left[\pi + 2\pi\int \frac{\text{Ramped Array from Start Freq. to Stop Freq.}}{\text{D/A Output Rate}}\right]$$

is simulated based on the start and stop frequency (Fstart and Fstop) of the swept frequency. The length of the ramped array between start and stop frequencies determines the number of data points in the final array. Steps 33 through 35 effectively implement the foregoing equation. In step 33, the starting and stopping points are represented by $$\frac{F\text{start}}{\text{Digitization Rate}}$$

$$\frac{F\text{stop}}{\text{Digitization Rate}}$$

In the example of FIGS. 3 and 5, these numbers would equal 0.025 and 0.1125, respectively. The difference between the starting and stopping points per cycle is offset by the starting point per cycle, which creates a sweep between the start and stopping cycles.

The result is integrated in step 34 as a running integral, multiplied by $2\pi$ and then shift by $\pi$ before the sine of the result is taken in step 35. The amplitude of the resulting signal is corrected so that the maximum amplitude corresponds to a value which is entered in step 31, or to a default value in the absence of an entry of ±2 volts according to step 36.

The simulated sine wave is then generated and printed to an ASCII file in step 37. With the aforementioned created linear swept wave, it is possible to complete the normalization step, per FIG. 8.

In step 41, as in the beginning step 31, requires that the user select a starting and stopping frequency for the swept waveform, a digitization rate representing the digital to analog computer speed in the digital to analog card 15 and a maximum amplitude for the swept signal. The swept wave is applied to the transducers 11 and 12 coupled together in accordance with the circuit described by the broken lines of FIG. 1.

The response of the swept wave applied to the combination of transducers 11 and 12 is acquired in step 24 of FIG. 6 is retrieved from the ASYST data file of computer 14 in step 42. A Fast Fourier Transform analysis is made in step 43 on the response. The resulting Fourier array is truncated to include a sub-array which begins at the starting frequency and ends at the stopping frequency in step 44. The truncated array is normalized to approximately 1.0 by dividing the average value of the array by each point in the array to derive a new array.

The result is subjected to a least square polynomial curve fit of a selected order in step 46. In accordance with a preferred embodiment, a fourth order polynomial was selected and the coefficients determined for the polynomial. From the determined polynomial, an array of N size, wherein N represents the total number of points for the swept wave, is created using the curve fit coefficients and the resulting array is stored as an array MULT in step 47.

Now that the correction data is available for equalizing the response of the transducers 11 and 12, step 33 through 35 recreate the initial wave in accordance with the provision of FIG. 7.

A step 48 will multiply the array obtained in step 47 with the initial wave generation data to derive a corrected swept frequency signal. The amplitude values are corrected in step 36 and the resulting corrected swept frequency signal is written to the ASCII file, replacing the original initial wave data of FIG. 7.

The steps 26, 27 and 28 of FIG. 6 may therefore be carried out and a signature derived for the test material 10.

Figure 9:
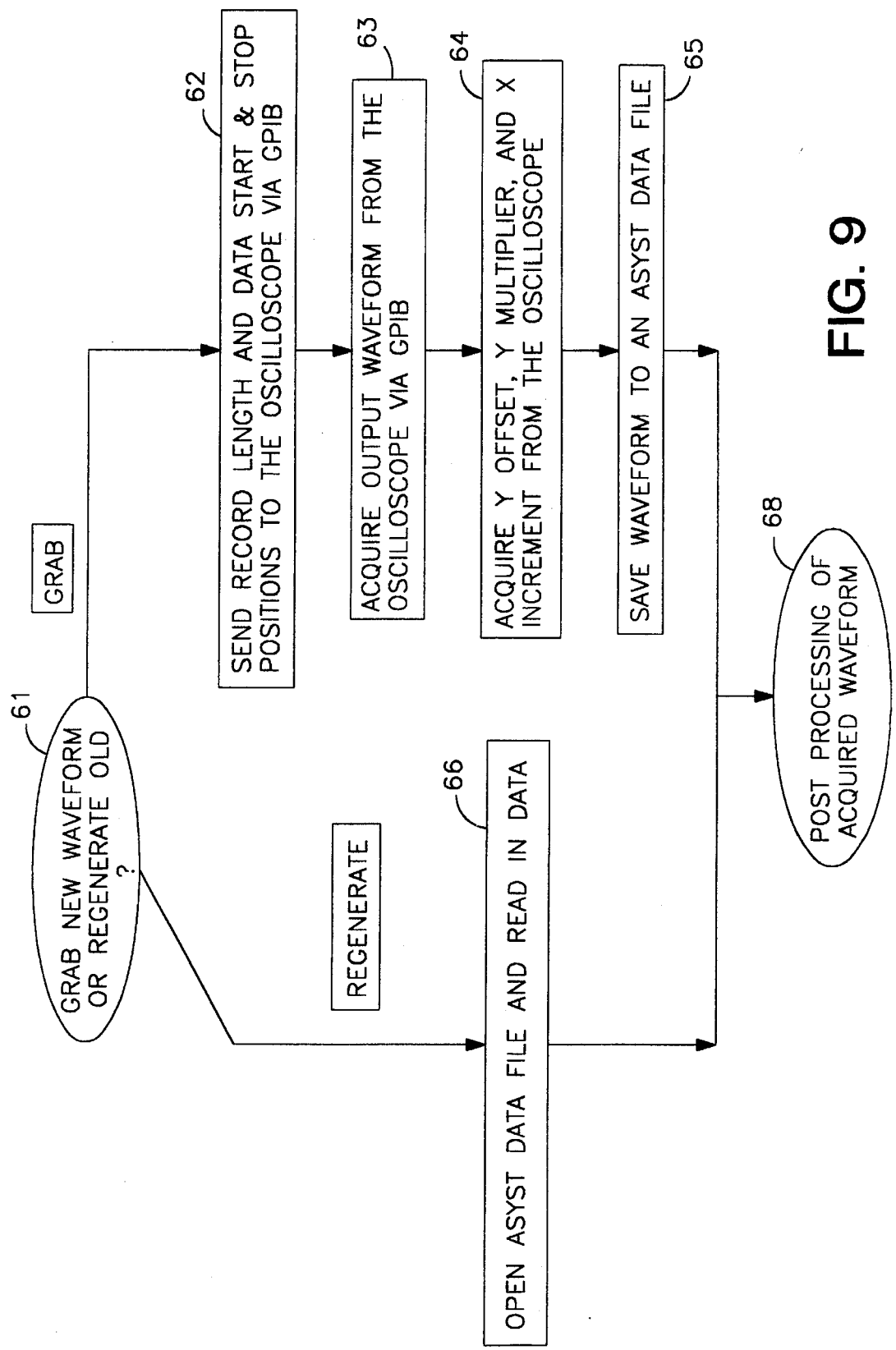
FIG. 9 illustrates the steps to form the GRAB WAVEFORM step of FIG. 6.

FIG. 9 illustrates how the step of grabbing the waveform for material analysis in steps 24 and 28 is performed. Referring now to FIG. 9, a menu selection is given to the user to either grab a new waveform or regenerate waveforms which were previously stored in the ASYST data file of computer 14.

For an initial test session, the grab mode will be selected by the user, and in step 62, the record length and data start and stop positions will be sent to the oscilloscope via the GPIB communication interface 15. The output waveform obtained from the oscilloscope as well as offsets, multiplication factors and time increments for each of the data points are obtained from the oscilloscope 64, via the GPIB interface in steps 63 an 64.

The retrieved waveform is saved to an ASYST data file in the computer 14. The resulting swept response obtained from the test part 10 is available for post processing in step 68, which may include the determination of a Fast Fourier Transform for the recovered swept waveform. Alternatively, the data may be saved until a test session is complete and then applied to the post processing step 68.

In this latter scenario, in step 61 the user will select the regenerate option, and at that time open the ASYST data file in step 66. The contents of the ASYST data file 66 are then subject to the post processing in step 68.

The recovered data represents a complete response to the swept frequency acoustic wave and is preserved in both phase and amplitude. The response is obtained with a single generation of the swept frequency acoustic wave which represents the entire frequency response over the swept frequency range. The system offers the ability to make assessments about the material from both amplitude as well as phase of the recovered signal spectral components.

Figure 10A:
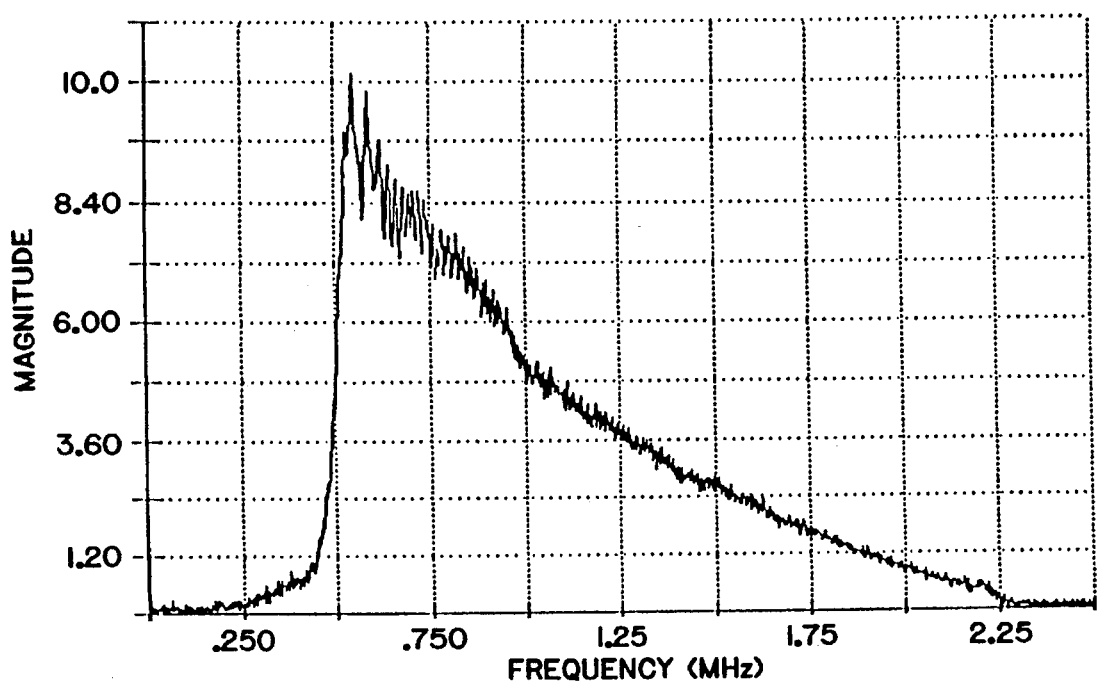
FIG. 10a illustrates a broadband spectral signature of one material in an area where no porosity defect exists using the preferred embodiment.
Figure 11:
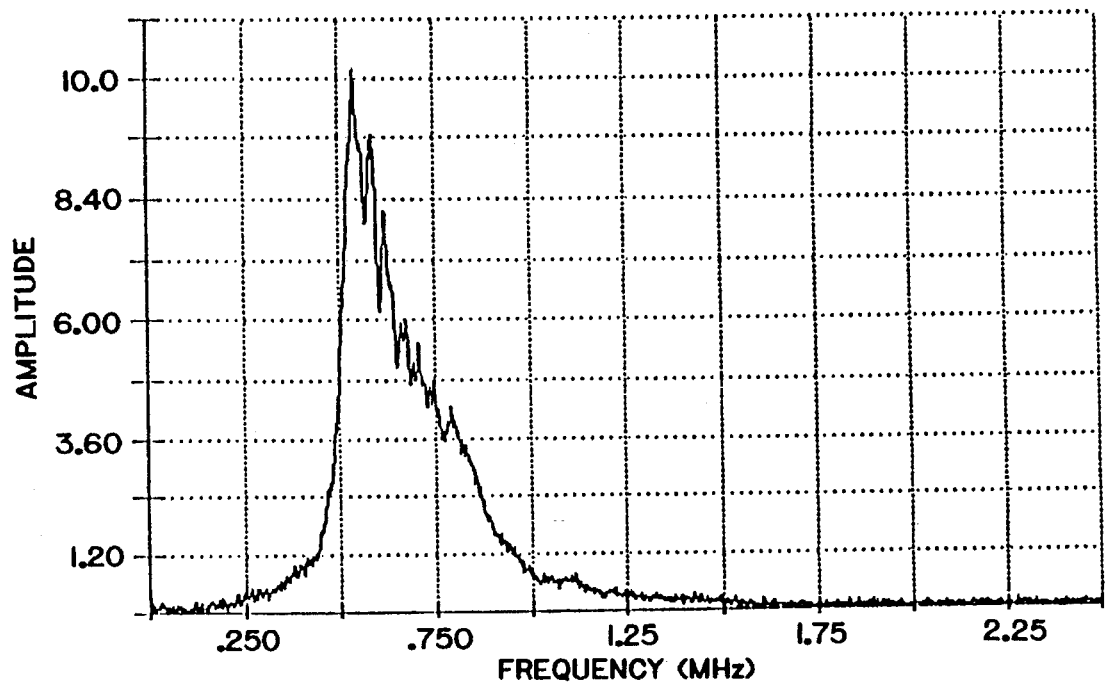
FIG. 11 illustrates the spectral response of the material of FIG. 10b in the area of the porosity defect.
Figure 10B:
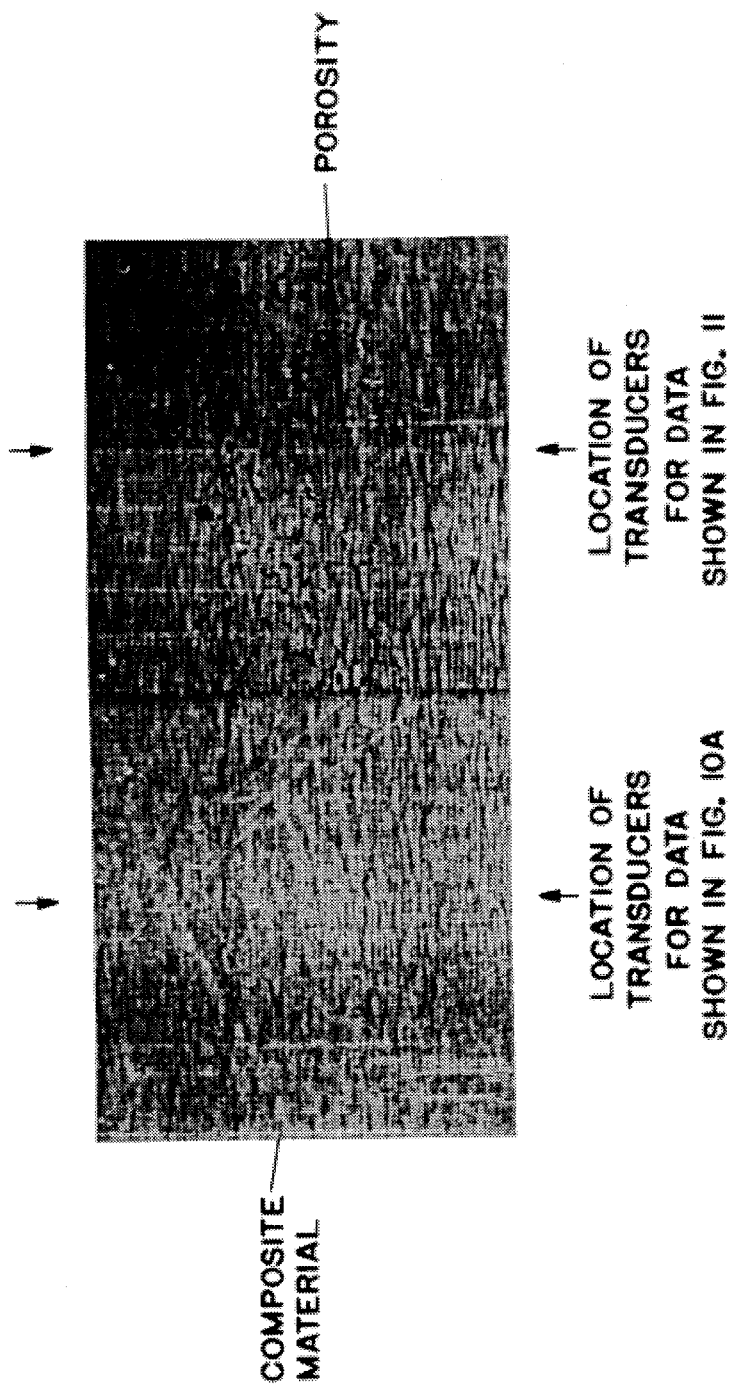
FIG. 10b illustrates a section view of the material tested having a porosity defect.

Using the foregoing procedures, a frequency spectrum signature may be obtained. FIGS. 10a and 11 represent the spectrum obtained from a material which has a porosity defect. This material is shown in FIG. 10b along with the relative placement of transducers 11 and 12 to obtain each signature. One signature shown in FIG. 10a represents the no defect portion, while the signature shown in FIG. 11 illustrates the signature of the portion having the porosity defect.

Figure 12A:
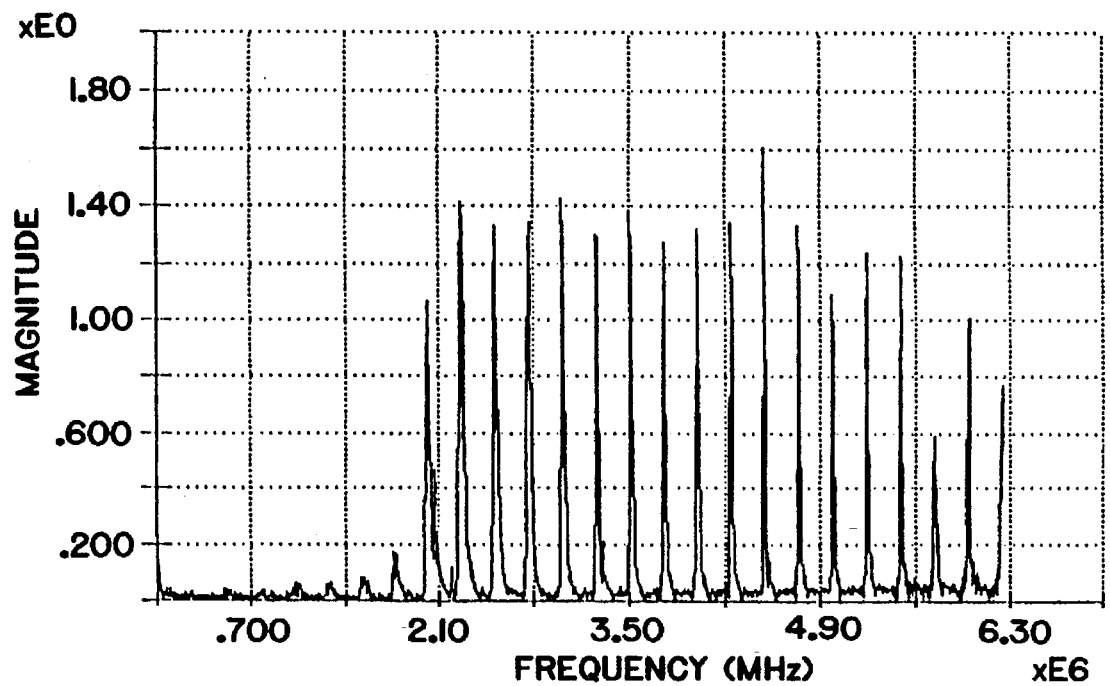
FIG. 12a illustrates yet another frequency response for a steel plate having machined near and reflective surfaces in accordance with FIG. 12b.
Figure 12B:
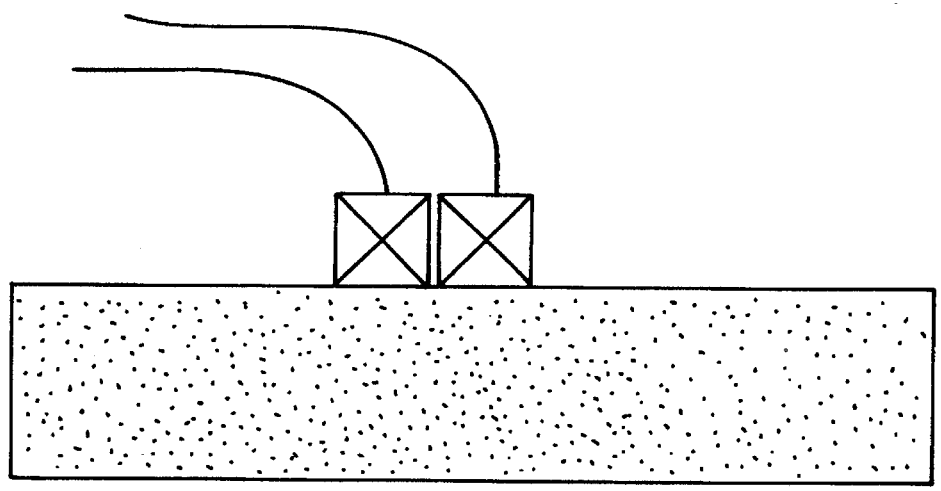
Figure 13A:
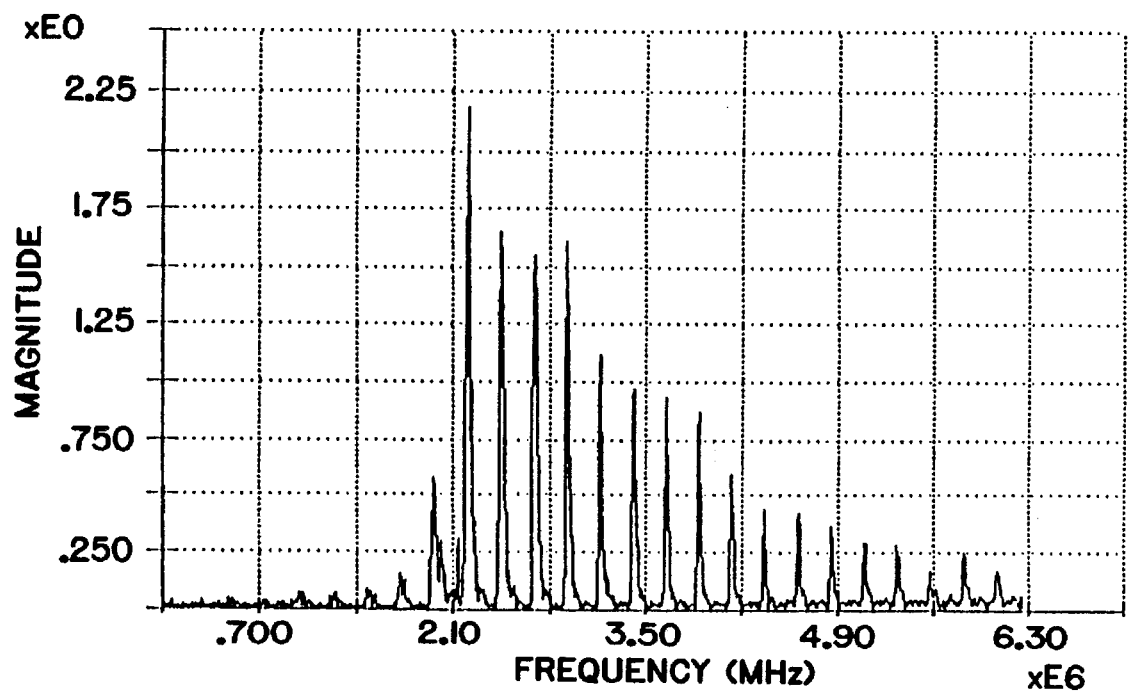
FIG. 13a illustrates another frequency response obtained from a steel plate having a machined near-surface and an oxidized reflection surface.
Figure 13B:
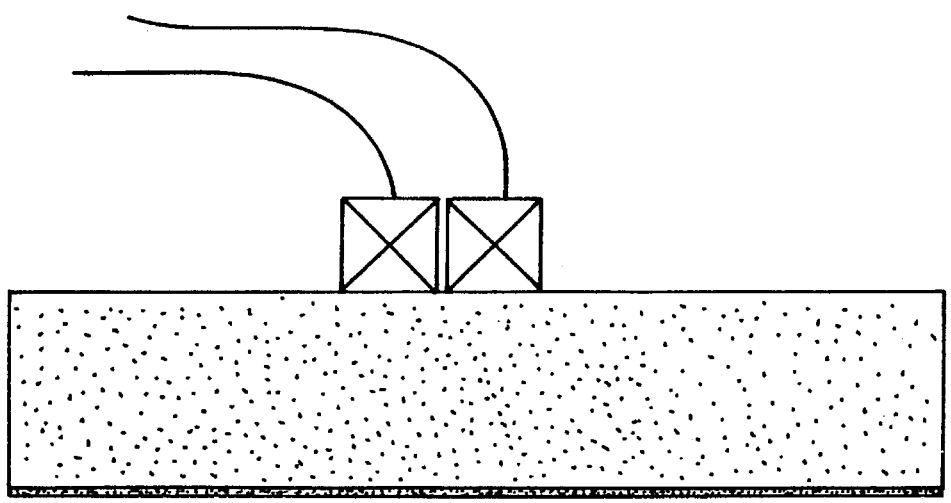

FIGS. 12a and 13a show U.S. scans from 2.0 to 7.0 MHz on a ±0.5" steel plate. In both cases, the surface facing the transducer was machined smooth. In FIG. 12b, the back surface was also machined smooth and as can be seen in the FFT of FIG. 12a, the entire frequency input range was carried nearly uniformly, meaning that all frequencies reflected equally well off the back surface. In FIG. 13b, the back surface was oxidized with the resulting reflection FFT as shown. The conclusion is that the higher frequencies were dispersed or preferentially absorbed by the rust. Hence, the ability to detect hidden surface conditions. One note on FIGS. 12a and 13a is that the FFTs are dominated by resonance peaks such that attenuation is actually tracked via the heights of these peaks. These peaks are the result of constructive interference and are expected and mathematically predictable for thin plates with good acoustic transmission characteristics.

It is clear from the respective signatures obtained in FIGS. 10, 11, 12a and 13a that various attributes may be ascribed to the test samples under examination.

The foregoing procedure is not time-consuming, nor does it require correlation between input and output signals. It also avoids the disadvantage of the prior art narrow pulse technique which, as mentioned previously, is subject to noise limitations imposed on the recovered signal from the test part.

Thus, there has been described with regard to one embodiment of the invention, an apparatus and method for performing ultrasonic testing on a test material. Those skilled in the art will recognize yet other embodiments as described by the claims which follow.

What is claimed is:

1. An apparatus for performing ultrasonic spectroscopy testing on a test material comprising:

a transmit transducer for coupling a swept frequency acoustical wave to a test material;

a sweep generator for supplying a frequency swept signal to said transmit transducer, said sweep generator comprising:

means for specifying a plurality of amplitude values of a signal which define each cycle of a swept wave for a swept frequency range having a start frequency and end frequency; and, means for continuously producing said amplitude values defining each cycle of said swept wave at a controlled rate, whereby a series of amplitude values are sequentially produced defining each cycle constituting said swept wave;

a receive transducer coupled to receive an acoustical wave from said material and produce an electrical signal in response thereto; and a digital processing device for storing said electrical signal representing an amplitude and phase of a spectral response to said swept frequency acoustic wave.

2. The apparatus for performing ultrasonic testing of claim 1, wherein said swept wave is defined by amplitude values which equalize the response of said transmit and receive transducers.

3. The apparatus for performing ultrasonic spectroscopy of claim 1, wherein said swept wave is defined by a non-linear varying sweep rate which equalizes the response of said transmit and receive transducers.

4. The apparatus of claim 1, wherein said digital processing device creates a Fast Fourier Transform of said swept acoustic wave response.

5. The apparatus of claim 1, wherein said swept wave is created by a digital to analog converter connected to a computer, programmed to perform the steps of:

generating an array of linearly increasing angles that are integrated; and generating an array of amplitude levels by taking the sine of said integrated angles.

6. An apparatus for performing ultrasonic testing on a test material comprising:

a transmit transducer for coupling a swept frequency acoustical wave to a test material;

a sweep generator for supplying a frequency swept signal to said transmit transducer, said sweep generator comprising:

a computer having a data file specifying a plurality of amplitude values which define each cycle of a swept wave having a start and end frequency;

a digital to analog converter for receiving said plurality of amplitude values and creating a swept analog signal from said values comprising each of said cycles between said start and end frequencies;

an amplifier connected to said digital to analog converter, and to said transmit transducer for supplying a signal to said transmit transducer to generate said swept acoustic wave.

7. The apparatus for performing ultrasonic testing of claim 6 further comprising:

a receive transducer for coupling an acoustical wave from said material; and, a digital processing device for storing an electrical signal representing said acoustic wave.

8. The apparatus for performing ultrasonic testing of claim 7, wherein said swept wave is defined by amplitude values which equalize the response of said transmit and receive transducers.

9. The apparatus of claim 7, wherein said digital processing device creates a Fast Fourier Transform of a detected swept acoustic wave from the amplitude and phase information contained in said electrical signal from said receive transducer.

10. The apparatus of claim 6, wherein said computer creates a from an array of angles and provides to said analog to digital converter a value of the sine of said angles at a linear rate, and creates a sweep of said sine of said angles by integrating each value of said array.

11. A method for performing ultrasonic testing on a test material comprising:

coupling an acoustic wave between a transmit transducer and a receive transducer;

measuring the frequency response of said transmit and receive transducers;

creating a data file comprising a plurality of cycles of a frequency sweep signal having a start frequency and a stop frequency which is equalized in amplitude accordance with said transmit and receive transducer's frequency response;

generating an analog sweep signal including said cycles, beginning and ending at said start and stop frequencies from said data file;

exciting said transmit transducer with said sweep signal when said transmit transducer is coupled to said test material;

detecting with said receive transducer an acoustic wave in said test material; and, analyzing the amplitude and phase of said detected swept acoustic wave from said test material.

12. The method of claim 11, wherein said analyzing step computes a Fast Fourier Transform of said detected sweep signal.

13. The method of claim 12, wherein said data file of a frequency sweep signal is produced by:

forming an array of increasing angles;

taking the sine of each angle of the array; and, applying the sine of each angle of the array to a digital to analog converter.

* * * * *